United States Patent
Mossaad et al.

(10) Patent No.: US 9,265,830 B2
(45) Date of Patent: Feb. 23, 2016

(54) IMPLANTABLE COMPOSITIONS AND METHODS FOR PREPARING THE SAME

(75) Inventors: Christina Mossaad, Holly Springs, NC (US); Lawrence A. Shimp, Morganville, NJ (US); Guobao Wei, Milltown, NJ (US); John Winterbottom, Dundee, MI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 521 days.

(21) Appl. No.: 13/090,745

(22) Filed: Apr. 20, 2011

(65) Prior Publication Data

US 2012/0269892 A1 Oct. 25, 2012

(51) Int. Cl.
| | |
|---|---|
| *A61K 47/10* | (2006.01) |
| *A61K 38/18* | (2006.01) |
| *A61K 9/00* | (2006.01) |
| *A61K 47/36* | (2006.01) |
| *A61K 9/06* | (2006.01) |
| *A61K 35/32* | (2015.01) |
| *A61L 27/36* | (2006.01) |
| *A61L 27/54* | (2006.01) |

(52) U.S. Cl.
CPC .............. *A61K 47/10* (2013.01); *A61K 9/0024* (2013.01); *A61K 38/1875* (2013.01); *A61K 47/36* (2013.01); *A61L 27/3608* (2013.01); *A61L 27/54* (2013.01); *A61K 9/06* (2013.01); *A61K 35/32* (2013.01); *A61L 2300/412* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,072,764 A * | 2/1978 | Chess | 426/558 |
| 5,073,373 A | 12/1991 | O'Leary et al. | |
| 5,290,558 A | 3/1994 | O'Leary et al. | |
| 5,314,476 A | 5/1994 | Prewett et al. | |
| 5,352,715 A | 10/1994 | Wallace et al. | |
| 5,422,340 A | 6/1995 | Ammann et al. | |
| 5,446,091 A | 8/1995 | Rhee et al. | |
| 5,484,601 A * | 1/1996 | O'Leary et al. | 424/422 |
| 5,510,121 A | 4/1996 | Rhee et al. | |
| 5,510,396 A | 4/1996 | Prewett et al. | |
| 5,510,418 A | 4/1996 | Rhee et al. | |
| 5,752,974 A | 5/1998 | Rhee et al. | |
| 5,916,870 A * | 6/1999 | Lee et al. | 514/8.2 |
| 6,071,530 A | 6/2000 | Polson et al. | |
| 7,067,123 B2 | 6/2006 | Gomes et al. | |
| 7,189,392 B1 | 3/2007 | Kim et al. | |
| 7,235,107 B2 | 6/2007 | Evans et al. | |
| 7,357,947 B2 | 4/2008 | Nimni | |
| 2002/0098222 A1 | 7/2002 | Wironen et al. | |
| 2002/0192263 A1* | 12/2002 | Merboth et al. | 424/426 |
| 2005/0251149 A1 | 11/2005 | Wenz | |
| 2006/0204544 A1 | 9/2006 | Sunwoo et al. | |

(Continued)

FOREIGN PATENT DOCUMENTS

WO    WO 9101720 A1 *    2/1991

*Primary Examiner* — Carlos Azpuru
*Assistant Examiner* — Casey Hagopian
(74) *Attorney, Agent, or Firm* — Sorell Lenna & Schmidt LLP (57) ABSTRACT

Methods for forming implantable compositions are provided. In some embodiments, the methods include (i) providing a gel base, (ii) adding water and a hydrating agent to the gel base to form a mixture, (iii) reducing the water content of the mixture; and (iv) adding a delivered material before, during, and/or after step (ii) or (iii). The water content is reduced to about 5% or less by weight of the implantable composition.

19 Claims, 1 Drawing Sheet

(56) References Cited

U.S. PATENT DOCUMENTS

| | | |
|---|---|---|
| 2006/0210643 A1 | 9/2006 | Truncale et al. |
| 2006/0263443 A1 | 11/2006 | Chow et al. |
| 2007/0003593 A1 | 1/2007 | Wironen et al. |
| 2007/0098756 A1 | 5/2007 | Behnam |
| 2007/0110820 A1 | 5/2007 | Behnam |
| 2007/0190101 A1 | 8/2007 | Yang et al. |
| 2007/0254041 A1* | 11/2007 | Drapeau et al. ............... 424/550 |
| 2007/0254042 A1 | 11/2007 | Drapeau et al. |
| 2007/0259814 A1 | 11/2007 | Lynch |
| 2008/0152691 A1 | 6/2008 | Drapeau et al. |
| 2008/0226688 A1 | 9/2008 | DePaula |
| 2008/0281431 A1 | 11/2008 | Missos |
| 2008/0299093 A1 | 12/2008 | Yang et al. |
| 2011/0112210 A1* | 5/2011 | Vogt et al. ..................... 523/116 |

\* cited by examiner

IMPLANTABLE COMPOSITIONS AND METHODS FOR PREPARING THE SAME

BACKGROUND

Overview of Grafts for Bone Repair

Implantable materials are used in a variety of applications, often to repair or replace tissue. Implantable materials are of particular interest in the repair of bone defects. The rapid and effective repair of bone defects caused by injury, disease, wounds, or surgery has long been a goal of orthopedic surgery. Toward this end, a number of compositions and implantable materials have been used or proposed for use in the repair of bone defects. The biological, physical, and mechanical properties of the compositions and materials are among the major factors influencing their suitability and performance in various orthopedic applications.

Autologous cancellous bone ("ACB") long has been considered the gold standard for bone grafts. ACB includes osteogenic cells, which have the potential to assist in bone healing, is nonimmunogenic, and has structural and functional characteristics that should be appropriate for a healthy recipient. Some people do not have adequate amounts of ACB for harvesting. These people include, for example, older people and people who have had previous surgeries. Further, there is reluctance to harvest ACB because of pain at the harvest site and donor morbidity.

Much effort has been invested in the identification and development of alternative bone graft materials. Urist has published seminal articles on the theory of bone induction and a method for decalcifying bone, i.e., making demineralized bone matrix (DBM). Urist M. R., Bone Formation by Autoinduction, Science 1965; 150(698):893-9; Urist M. R. et al., The Bone Induction Principle, Clin. Orthop. Rel. Res. 53:243-283, 1967. DBM is an osteoinductive material, in that it induces bone growth when implanted in an ectopic site of a rodent, owing to the osteoinductive factors contained within the DBM. Honsawek et al. (2000). There are numerous osteoinductive factors, e.g., BMP 1-18, which are part of the transforming growth factor-beta (TGF-beta) superfamily. BMP-2 has been widely studied. There are also other proteins present in DBM that are not osteoinductive alone but still contribute to bone growth, including fibroblast growth factor-2 (FGF-2), insulin-like growth factor-I and -II (IGF-I and IGF-II), platelet derived growth factor (PDGF), and transforming growth factor-beta 1 (TGF-beta.1). (Hauschka, et al. 1986; Canalis, et al, 1988; Mohan et al. 1996.)

Various cocktails of growth factors have been measured in DBM, including BMP2, TGFβ1, FGFa, IGF-I, PDGF, VEGF (Wildemann et al, 2007), BMP4 (Blum et al, 2004 and Honsaweket et al, 2005), and BMP7 (Pietrzak et al, 2006). Other extracellular matrix proteins have also been measured, including type I collagen, fibronection, Bone Sialoprotein (BSP), and osteopontin (Shigeyama et al, 1995). Combinations of growth factors may be more osteoinductive than a single growth factor (Kawai et al, 2006, Mehlhorn et al, 2007, Shintani et al, 2007, Raiche et al, 2004 and Ripamonti et al, 1997). DBM extracellular matrix proteins such as collagen may be used as carriers for the growth factors (Reddi et al, 2000).

DBM implants have been reported to be particularly useful (see, for example, U.S. Pat. Nos. 4,394,370, 4,440,750, 4,485,097, 4,678,470, and 4,743,259; Mulliken et al., *Calcif Tissue Int* 33:71, 1981; Neigel et al., *Opthal. Plast. Reconstr. Surg.* 12:108, 1996; Whiteman et al., *J. Hand. Surg.* 18B:487, 1993; Xiaobo et al., *Clin. Orthop.* 293:360, 1993, each of which is incorporated herein by reference). Useful DBM implants are disclosed in U.S. Pat. Nos. 5,073,373; 5,284,655; 5,290,558; 5,314,476; 5,507,813; 5,510,396; and 5,676,146, each of which is incorporated by reference herein.

DBM may be derived from donated human tissue. The bone is removed aseptically and treated to kill any infectious agents. The bone is typically particulated by milling or grinding, and then the mineral component is extracted by various methods, such as by soaking the bone in an acidic solution. The remaining matrix is malleable and can be further processed and/or formed and shaped for implantation into a particular site in the recipient.

In some grafts, non-bone materials may be used, including hydroxyapatite, ceramics, calcium sulfate, calcium phosphates, tricalcium phosphate, bioactive glasses, other materials, and combinations of these.

In some applications, the graft material (which also may be referred to as a delivered material), which may include biologics and/or non-bone materials, are combined with a carrier. The delivered material-carrier combination then may be shaped into a suitable bone graft.

Carriers

Generally, a carrier may be employed to facilitate in vivo use and/or formation of a particular configuration of the implantable material. In considering carriers for combination with a delivered material, it is desirable to have a carrier that has minimal effect on bioactive compounds and/or biocompatible compounds of the delivered material. Suitable carriers may include, for example, glycerol or hydrogel. The specific carrier used may be selected based on desired handling characteristics and surgeon preference.

Hydrogels exhibit many properties that make them suitable carriers for implantable materials used in the repair of bone and other tissue defects. For example, hydrogels exhibit controlled viscosity over a wide range of values, strong resistance to surgical irrigation, and excellent biocompatibility. Hydrogels are formed of a highly absorbent natural or synthetic polymer base material dispersed in water. Water has been the universal solvent for hydrogels because those skilled in the art have not perceived disadvantages to the use of water, and because nonaqueous solvents for hydrogels have been thought impractical or impossible.

The inventors have determined that, while hydrogels may provide suitable or desirable handling characteristics to an implantable material, the presence of water may have deleterious effects on the bioactivity of the material, and/or on the material's shelf life. Accordingly, a process that adequately solubilizes or otherwise disperses the polymeric base material of a hydrogel in a nonaqueous solvent, or a water substitute, but which produces a material having similar or superior physical and biologic properties to hydrogels as a carrier, is desirable. The have developed, and disclose herein, a method for preparing a hydrogel carrier that has a substantial absence of water.

SUMMARY

Methods for forming implantable compositions are provided herein. In some embodiments, the methods include (i) providing a gel base, (ii) adding water and a hydrating agent to the gel base to form a mixture, (iii) reducing the water content of the mixture; and (iv) adding a delivered material before, during, and/or after step (ii) or (iii). The water content is reduced to about 5% or less by weight of the implantable composition.

Implantable compositions are also provided. The implantable compositions include a delivered material and a carrier.

The carrier includes a gel base and a hydrating agent. A water content of the implantable composition is less than about 5% by weight of the composition.

The implantable compositions may be formed and used in any of a variety of desirable manners. For example, the implantable composition may be formed into an osteoimplant and applied at a bone repair site, or at a site for bone augmentation or ectopic bone formation (e.g., lateral spine fusion). Further examples of the use of the implantable compositions disclosed herein include at bone or other tissue sites that have been injured, or that have defects brought about during the course of surgery, disease, trauma, malignancy, or developmental malformation.

This application refers to various patents, patent applications, journal articles, and other publications, all of which are incorporated herein by reference. The following documents are incorporated herein by reference: PCT/US04/43999; PCT/US05/003092; US 2003/0143258 A1; PCT/US02/32941; *Current Protocols in Molecular Biology, Current Protocols in Immunology, Current Protocols in Protein Science, and Current Protocols in Cell Biology*, John Wiley & Sons, N.Y., edition as of July 2002; Sambrook, Russell, and Sambrook, *Molecular Cloning: A Laboratory Manual*, 3rd ed., Cold Spring Harbor Laboratory Press, Cold Spring Harbor, 2001; Rodd 1989 "Chemistry of Carbon Compounds," vols. 1-5 and supps., Elsevier Science Publishers, 1989; "Organic Reactions," vols. 1-40, John Wiley and Sons, New York, N.Y., 1991; March 2001, "Advanced Organic Chemistry," 5th ed. John Wiley and Sons, New York, N.Y. In the event of a conflict between the specification and any of the incorporated references, the specification shall control. Where numerical values herein are expressed as a range, endpoints are included.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed description is to be regarded as illustrative in nature and not restrictive.

BRIEF DESCRIPTION

DEFINITIONS

Bioactive Agent is used herein to refer to a compound or entity that alters, inhibits, activates, or otherwise affects biological or chemical events. For example, bioactive agents may include, but are not limited to, osteogenic or chondrogenic proteins or peptides (including the osteoinductive or growth factors described above and synthetic and recombinant version of these, including recombinant human bone morphogenetic protein (rhBMP-2), available from Medtronic, Inc., as INFUSE® Bone Graft, and bone morphogenetic protein-7 (rhBMP-7 or Osteogenic Protein 1), available from Olympus Biotech Corp. in its OP-1 products), anti-AIDS substances, anti-cancer substances, antibiotics, immunosuppressants, anti-viral substances, enzyme inhibitors, hormones, neurotoxins, opioids, hypnotics, anti-histamines, lubricants, tranquilizers, anti-convulsants, muscle relaxants and anti-Parkinson substances, anti-spasmodics and muscle contractants including channel blockers, miotics and anti-cholinergics, anti-glaucoma compounds, anti-parasite and/or anti-protozoal compounds, modulators of cell-extracellular matrix interactions including cell growth inhibitors and antiadhesion molecules, vasodilating agents, inhibitors of DNA, RNA or protein synthesis, anti-hypertensives, analgesics, anti-pyretics, steroidal and non-steroidal anti-inflammatory agents, anti-angiogenic factors, angiogenic factors, anti-secretory factors, anticoagulants and/or antithrombotic agents, local anesthetics, ophthalmics, prostaglandins, anti-depressants, anti-psychotic substances, anti-emetics, and imaging agents. In certain embodiments, the bioactive agent is a drug. Bioactive agents further include RNAs, such as siRNA, and osteoclast stimulating factors. In some embodiments, the bioactive agent may be a factor that stops, removes, or reduces the activity of bone growth inhibitors. In some embodiments, the bioactive agent is a growth factor, cytokine, extracellular matrix molecule or a fragment or derivative thereof, for example, a cell attachment sequence such as RGD. A more complete listing of bioactive agents and specific drugs suitable for use in the present invention may be found in "Pharmaceutical Substances: Syntheses, Patents, Applications" by Axel Kleemann and Jurgen Engel, Thieme Medical Publishing, 1999; the "Merck Index: An Encyclopedia of Chemicals, Drugs, and Biologicals", Edited by Susan Budavari et al. CRC Press, 1996; and the United States Pharmacopeia-25/National Formulary-20, published by the United States Pharmcopeial Convention, Inc., Rockville Md., 2001, each of which is incorporated herein by reference.

Biocompatible, as used herein, is intended to describe materials that, upon administration in vivo, do not induce undesirable long-term effects.

Bone as used herein refers to bone that is cortical, cancellous or cortico-cancellous of autogenous, allogenic, xenogenic, or transgenic origin.

Bone particles herein refers to relatively small bone pieces such as fibers, bundles of loosely connected fibers, threads, narrow strips, thin sheets, chips, shards, particles, powders, other shapes, etc., that possess regular, irregular, or random geometries and which can be separated form each other to any desired extent. While description herein may be made specifically to bone fibers in some embodiments, as noted it is to be appreciated that bone fibers are merely one type of particle that may be used with the implantable compositions disclosed herein.

Demineralized, as used herein, refers to any material generated by removing mineral material from tissue, e.g., bone tissue. In certain embodiments, the demineralized compositions described herein include preparations containing less than 8%, less than 5%, or less than 1% calcium by weight. Partially demineralized bone (e.g., preparations with greater than 5% calcium by weight but containing less than 100% of the original starting amount of calcium) is also considered within the scope of the invention. In some embodiments, demineralized bone has less than 95% of its original mineral content. Demineralized is intended to encompass such expressions as "substantially fully demineralized," "substantially demineralized," "partially demineralized," and "fully demineralized."

Demineralized bone matrix or DBM, as used herein, refers to any material generated by removing mineral material from bone tissue. In some embodiments, the DBM compositions as used herein include preparations containing less than 8%, less than 5%, or less than 1% calcium by weight. Partially demineralized bone (e.g., preparations with greater than 5% calcium by weight but containing less than 100% of the original starting amount of calcium) are also considered within the scope of the invention.

Osteoconductive is used herein to refer to the ability of a non-osteoinductive substance to serve as a suitable template or substance along which bone may grow.

Osteogenic is used herein to refer to the ability of an agent, material, or implant to enhance or accelerate the growth of new bone tissue by one or more mechanisms such as osteogenesis, osteoconduction, and/or osteoinduction.

Osteoinductive, as used herein, refers to the quality of being able to recruit cells from the host that have the potential to stimulate new bone formation. Any material that can induce the formation of ectopic bone in the soft tissue of an animal is considered osteoinductive. Most osteoinductive materials induce bone formation in athymic rats when assayed according to the method of Edwards et al., "Osteoinduction of Human Demineralized Bone: Characterization in a Rat Model," *Clinical Orthopaedics & Rel. Res.*, 357:219-228, December 1998, incorporated herein by reference. In other instances, osteoinduction is considered to occur through cellular recruitment and induction of the recruited cells to an osteogenic phenotype.

Osteoinductivity score, as used herein, refers to a score ranging from 0 to 4 as determined according to the method of Edwards et al. (1998) or an equivalent calibrated test. In the method of Edwards et al. a score of "0" represents no new bone formation; "1" represents 1%-25% of the implant being involved in new bone formation; "2" represents 26-50% of the implant being involved in new bone formation; "3" represents 51%-75% of the implant being involved in new bone formation; and "4" represents greater than 75% of the implant being involved in new bone formation. In most instances, the score is assessed 28 days after implantation. However, the osteoinductivity score may be obtained at earlier time points, such as 7, 14, or 21 days following implantation. In these instances it may be desirable to include a normal DBM control such as DBM powder without a carrier, and, if possible, a positive control such as BMP. Occasionally, osteoinductivity also may be scored at later timepoints, such as 40, 60, or even 100 days following implantation. Percentage of osteoinductivity refers to an osteoinductivity score at a given time point expressed as a percentage of activity of a specified reference score.

DETAILED DESCRIPTION

I. Implantable Compositions

In various embodiments, the implantable compositions of the present disclosure may include a delivered material, and a carrier including a gel base and a hydrating agent. The delivered material may comprise or contain one or more bioactive compounds and/or biocompatible compounds. The water content of the carrier may be about 5% or less by weight of the implantable composition.

The inventors have determined that replacing the water in hydrogel carriers with a substitute, nonaqueous hydrating agent can increase the shelf life of an implantable composition, and can alter the handling characteristics of the implantable composition. It is believed that the presence of water in hydrogel carriers may have a deleterious effect on components often present the implantable material, particularly over time. For example, in some implants, DBM, or other material comprising or containing water-sensitive materials, may be provided in the hydrogel carrier. Such water-sensitive materials may comprise, for example, proteins, growth factors, other biomaterials, bioglass, tricalcium phosphate, or a resorbable polymer. The water in the hydrogel may degrade such water-sensitive materials over time, thereby adversely affecting the stability and/or shelf-life of the implant.

As an alternative to water, other liquid wetting or hydrating agents having multiple negatively charged moieties may be used to solubilize or otherwise disperse the polymeric base material of a hydrogel. In this manner, the adverse effects of water on the stability of implantable products formed using hydrogels may be eliminated, reduced, or mitigated.

A. Bioactive and Biocompatible Compounds

The delivered material may be any material comprising or suitable for carrying bioactive compounds and/or biocompatible compounds. Depending on the delivered material selected, such bioactive compounds and/or biocompatible compounds may be endogenous to the material or may be exogenously added to the material. Any suitable material may be used, including, but not limited to, bone, other tissue, hydroxyapatite, ceramics, calcium sulfate, calcium phosphates, tricalcium phosphate, bioactive glasses, bioactive agents, other materials, and combinations of these.

a. Bioactive Compounds

In some embodiments, the implantable compositions of the present disclosure may include a delivered material comprising or containing bioactive agents, which may include bioactive compounds and/or biocompatible compounds.

Bioactive compounds may be endogenously present in the material carried by the hydrogel or exogenously added to the material carried by the hydrogel. Suitable bioactive compounds for the inventive compositions may include, for example, bone, other tissue, growth factors, glycoproteins, and/or other bioactive materials suitable for use in the repair of tissue or bone, such as chondroitin sulfate, and may include bioactive agents. Suitable growth factors may include recombinant human bone morphogenetic protein (rhBMP-2), available from Medtronic, Inc., as INFUSE® Bone Graft; bone morphogenetic protein-7 (rhBMP-7 or Osteogenic Protein 1), available from Olympus Biotech Corp. in its OP-1 products; other growth factors; anti-AIDS substances; anti-cancer substances; antibiotics; immunosuppressants; anti-viral substances; enzyme inhibitors; hormones; neurotoxins; opioids; hypnotics; anti-histamines; other materials; and combinations of these. Suitable growth factors also may include members of the TGF-β, IGF, and BMP protein families. As noted, the bioactive compounds may be endogenously present in a material of the implantable compositions, as in the case of bone or bone-derived elements (e.g., demineralized bone), may be exogenously added to the implantable composition, may be combinations of endogenous and exogenous bioactive compounds, etc.

Biocompatible Compounds

In various embodiments, in addition to or in lieu of bioactive agents, the delivered material may comprise or contain one or more biocompatible compounds. Suitable biocompatible compounds may include, for example, bioactive glass or bioglass, hydroxyapatite, ceramics, calcium sulfates, calcium phosphates, tricalcium phosphate, polymers (e.g., porous polymers, resorbable polymers), 1,2,3-trichloropropane, metal particles (e.g., titanium, shape-memory alloys), and/or other biocompatible materials suitable for use in the repair of tissue or bone.

c. Bone

In a specific embodiment, the delivered material may be bone or bone derived elements. The bone may be a bioactive agent, or not. The bone may be obtained utilizing methods well known in the art, e.g., allogenic donor bone. Generally, the bone can be nondemineralized, partially demineralized (including surface demineralized), demineralized, deorganified, anorganic, or combinations thereof.

The bone or bone-derived elements can be readily obtained from donor bone by various suitable methods, e.g., as described in U.S. Pat. No. 6,616,698, incorporated herein by reference. Autogenic, allogenic, xenogenic, or transgenic bone can be used. Suitable types of xenogenic bone may include porcine, equine, or bovine. The bone can be cortical, cancellous or corticocancellous. In specific embodiments described herein, the bone is cortical allogenic bone, e.g., femur, tibia, fibula, radius, ulna, etc.

The bone suitable for use in the implantable compositions herein are not limited to any size or configuration of bone to be treated. Bone utilized as the starting, or stock, material may range in size from relatively small pieces of bone to bone of such dimensions as to be recognizable as to its anatomical origin to whole bone. For example, the stock material may range from fragments to whole bone and the formed bone composition may range from particles to fibers to plates. In some embodiments, the whole bone may be partially subdivided, such as into strips, for further processing by methods disclosed herein.

Separating the bone (or separation), also referred to as particulation, refers to subdivision of the bone. Separating the bone may provide space and surface area for cellular activity (osteoconductivity). Separating the bone may further expose bone inducing/facilitating proteins to induce bone regeneration (osteoinductivity). Generally, separation may be done in a manner such that the bone subdivides in a manner generally consistent with natural morphology. In some embodiments, separation may be used to subdivide the bone into bone particles, fibers, plates, or other desired configuration and size. In some embodiments, separation may be used to subdivide the bone into bone fibers. Thickness and width of the fibers may be generally equal and length of the fibers may be up to the length of the stock material.

Separation may be done by any suitable technique. For example, machines or instruments that cut, shred, mill, extrude, and/or chop may be used. Examples of suitable equipment may use a sharp bit or blade on or into the bone to cut or mill the bone, including by cutting away material that is not in the desired configuration (such as material that is not fibrous). For example, mills, including ball mills, impact mills, grating mills, shearing mills, and cutting mills, may be used.

d. Demineralized Bone

In some embodiments, the delivered material may comprise demineralized bone. DBM preparations have been used for many years in orthopedic medicine to promote the formation of bone. For example, DBM has found use in the repair of fractures, in the fusion of vertebrae, in joint replacement surgery, and in treating bone destruction due to underlying disease such as a bone tumor. DBM is has been shown to promote bone formation in vivo by osteoconductive and osteoinductive processes. The osteoinductive effect of implanted DBM compositions results from the presence of active growth factors present on the isolated collagen-based matrix. These factors include members of the TGF-β, IGF, and BMP protein families. Particular examples of osteoinductive factors include TGF-β, IGF-1, IGF-2, BMP-2, BMP-7, parathyroid hormone (PTH), and angiogenic factors. Other osteoinductive factors such as osteocalcin and osteopontin are also likely to be present in DBM preparations as well. There are also likely to be other unnamed or undiscovered osteoinductive factors present in DBM.

For use in the compositions of the present invention, the bone may be demineralized in any suitable manner. Generally, demineralization procedures remove the inorganic mineral component of bone by employing acid solutions, referred to as an acid treatment. Such procedures are well known in the art, see for example, Reddi et al., Proceeding of the National Academy of Sciences of the United States of America 69, pp. 1601-1605 (1972), incorporated herein by reference. The strength of the acid solution, the shape and size of the bone and the duration of the demineralization procedure influence the extent of demineralization and may be selected for the particular application. Generally speaking larger bone portions as compared to small particles require more lengthy and vigorous demineralization. For example, small fibers may be demineralized within approximately 3 hours while large fibers may be demineralized within approximately 4 hours. Guidance for specific parameters for demineralization and for the demineralization of different size bone can be found in U.S. Pat. No. 5,846,484, Harakas, Clinical Orthopaedics and Related Research, pp 239-251 (1983) and Lewandrowski et al., Journal of Biomedical Materials Research, 31, pp. 365-372 (1996), and U.S. Pat. Nos. 6,189,537 and 6,305,379, each of which is incorporated by reference herein. U.S. patent application Ser. No. 12/849,054, filed Aug. 3, 2010, discloses suitable methods for demineralization that may be used in accordance with the present invention and is herein incorporated by reference in its entirety.

After acid treatment, the demineralized bone may be rinsed with sterile water for injection or sterile purified water to remove residual amounts of acid.

B. Carriers

In illustrative embodiments, the delivered material of the implantable compositions may be provided in a carrier. Generally, a carrier may be employed to facilitate in vivo use and/or formation of a particular configuration of the implantable configuration.

In some embodiments, the carrier may include a non-aqueous, or substantially non-aqueous, gel. As used herein, the term gel may refer to a solid, polymeric material (hereinafter, "gel base") that is at least partially solubilized in, or otherwise dispersed in, a liquid (hereinafter, "hydrating agent"). Suitable gel bases may include chitosan, alginate, hyaluronic acid, polyvinyl alcohols, polyvinyl pyrolidone, dextran, carboxymethyl cellulose, collagen, starches, gelatin, extracted proteins, starches, any other water soluble polymeric materials, and/or combinations thereof. Specific forms of hyaluronic acid as carriers for demineralized bone are described in U.S. Pat. No. 6,030,635, incorporated by reference herein. Suitable hydrating agents may include any liquids which can be substituted for water to at least partially solubilize a gel base. For example, hydrating agents may include liquid polyhydroxy compounds such as glycerol, low molecular weight polyethylene glycol, high molecular polyethylene glycol, and/or any other liquids having multiple negatively charged moieties, and combinations thereof. Suitable polyhydroxy compounds are listed in U.S. Pat. No. 5,290,558, previously incorporated by reference herein.

C. Additives

Optionally, other additives, including bioactive agents, may be included in the implantable compositions disclosed herein. It will be appreciated that the amount of additive used may vary depending upon the type of additive, the specific activity of the particular additive preparation employed, and the intended use of the composition. The desired amount may be readily determinable by the user. Any of a variety of medically and/or surgically useful optional substances can be incorporated in, or associated with, the osteoinductive factors either before, during, or after preparation of the osteogenic composition.

In certain embodiments, the additive is adsorbed to or otherwise associated with the implantable composition. The additive may be associated with the implantable composition through specific or non-specific interactions, or covalent or noncovalent interactions. Examples of specific interactions include those between a ligand and a receptor, an epitope and an antibody, etc. Examples of nonspecific interactions include hydrophobic interactions, electrostatic interactions, magnetic interactions, dipole interactions, van der Waals interactions, hydrogen bonding, etc. In certain embodiments, the additive is attached to the implantable composition, for example, to the carrier, using a linker so that the additive is free to associate with its receptor or site of action in vivo. In other embodiments the additive is either covalently or non-covalently attached to the carrier. In certain embodiments, the additive may be attached to a chemical compound such as a peptide that is recognized by the carrier. In another embodiment, the additive is attached to an antibody, or fragment thereof, that recognizes an epitope found within the carrier. In certain embodiments at least additives are attached to the implantable composition. In other embodiments at least three additives are attached to the implantable composition. An additive may be provided within the implantable composition in a sustained release format. Thus, delivery of a growth factor in an implantable composition may include micro- or nano-encapsulation. For example, the additive may be encapsulated within biodegradable nanospheres, microspheres, etc. In this method, a growth factor (or other bioactive agent) is first encapsulated in a suitable material, such as a bioresorbable polymer or hydrogel micro- or nano-particle. The encapsulated growth factor then is immobilized onto or into the implantable composition. The bioresorbable polymer/hydrogel may be designed to control release kinetics of the growth factor.

It will be understood by those skilled in the art that the lists of optional substances herewith included are not intended to be exhaustive and that other materials may be admixed with the delivered materials within the practice of the present invention.

Radiopaque substances may be added to impart radiopacity to the composition. Examples of substances imparting radiopacity include for example, bone particles that have not been fully demineralized, including mineralized cancellous bone, mineralized cortical bone, and partially demineralized bone in solid, particle, or fiber form; Barium- and Iodine-containing compounds or compositions, e.g., Barium Sulfate and Barium Sulfate for Suspension; Iopanoic Acid; and the like. U.S. Pat. No. 5,676,146 discusses radiopaque implantable materials and is herein incorporated by reference in its entirety.

Development of a vasculature around the implant site may also be beneficial in forming new bone and/or cartilage tissue. Angiogenesis may be a contributing factor for the replacement of new bone and cartilage tissues. In certain embodiments, angiogenesis may be promoted so that blood vessels are formed at the site to allow efficient transport of oxygen and other nutrients and growth factors to the developing bone or cartilage tissue. Thus, angiogenesis promoting factors may be included in the osteoimplant to increase angiogenesis in that region. For example, class 3 semaphorins, e.g., SEMA3, controls vascular morphogenesis by inhibiting integrin function in the vascular system, Serini et al. *Nature*, (July 2003) 424:391-397, incorporated herein by reference, and may be included in the osteoimplant. Vascular Endothelial Growth Factor (VEGF) and other cystine-knot growth factors may be used as well.

III. Methods of Preparing

Methods for preparing the implantable compositions of the present invention may include the substitution of a nonaqueous, liquid hydrating agent for water in a carrier, such as in a hydrogel material. This technique is useful for preparing non-aqueous solutions of materials in solvents that the materials do not directly dissolve in. For example, carboxy methylcellulose will not dissolve in glycerol even if the glycerol is heated. But carboxy methylcellulose, if first dissolved in water, can be converted to a glycerol solution by adding glycerol to the water solution of carboxy methylcellulose, then removing the water by a drying process, preferably involving vacuum. The substitution may be achieved by dissolving a gel base in water to form a mixture, adding a hydrating agent to the mixture, and reducing the water content of the mixture. Not to be limited in theory, it is believed that in the presence of water, the gel base has an "open" structure, which facilitates replacement of the O—H bonds of water with the hydroxide groups of a liquid hydrating agent as the water is removed during drying.

Another advantage of the process is that it allows the incorporation of a heat sensitive substance, such as BMP-2, into the hydrogel. Many base gel materials can only dissolve in water (or other solvent) by the application of heat. Starch, for example, has to be boiled in water to dissolve. With the solvent substitution technique, BMP-2 can be dissolved in water (at room temperature), then added to glycerol, and then the water/BMP-2/glycerol mixture can be combined with the hydrated starch. Lyophilization (or mild vacuum drying) will serve to incorporate the BMP-2 and glycerol with the starch while eliminating the water; resulting in a stable starch/glycerol/BMP-2 gel that could be used for bone grafting applications.

Figure 1:
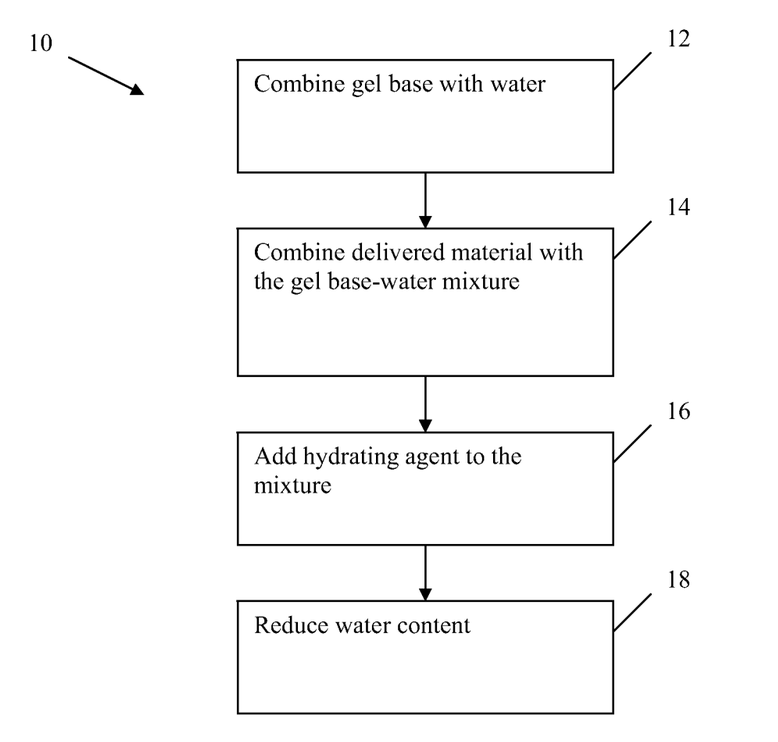
FIG. 1 illustrates a method of making an implantable composition in accordance with one embodiment of the present disclosure.

FIG. 1 illustrates a method of preparing an implantable composition in accordance with one embodiment of the present disclosure. In one embodiment, the method 10 may include combining a gel base with water to form a mixture [block 12]. Following the step of block 12, a delivered material may be combined with the gel base-water mixture of block 12 [block 14]. The delivered material may comprise or include one or more bioactive and/or biocompatible compounds. The method may then include adding a hydrating agent to the mixture of block 14 [block 16]. Alternatively, or additionally, the hydrating agent may be added in step 12 (e.g., in the form of a water-hydrating agent mixture). The hydrating agent may be added such that the hydrating agent is present in an amount ranging from about 1% to about 90% by weight of total liquid in the mixture (i.e., the water and the hydrating agent). Alternatively, the hydrating agent may be present in an amount ranging from about 1% to about 50% by weight of the total liquid in the mixture. In a further alternative, the hydrating agent may be present in an amount ranging from about 1% to about 10% by weight of the total liquid in the mixture.

Following the step of block 14, the water content of the mixture of block 16 may be reduced, thereby leaving a composition [block 18]. Reduction of the water content may be achieved by drying techniques. In one embodiment, reduction of the water content is accomplished by lyophilization or by vacuum drying. The water content may be reduced to about 5% or less by weight of the composition. Alternatively, the water content may be reduced to about 3% or less by weight of the composition. In a further alternative, the water content may be reduced to about 1% or less by weight of the composition.

In an alternative to the embodiment of FIG. 1, the addition of the delivered material (the step of block 14) may occur concomitantly with and/or subsequent to the step of block 16 and/or the step of block 18.

A. Formulation

The relative amounts of gel base, hydrating agent, and delivered material in the implantable compositions prepared utilizing the methods of the present disclosure may be selected such that the composition exhibits physical properties (e.g., deformability, viscosity, etc.) that are desired for the particular clinical application. For example, by varying the relative amounts of the components, the implantable compositions may be formulated to be settable, moldable, injectable, or the like.

In various embodiments, the implantable compositions may be formulated such that compositions include about 20 to about 90 percent by weight gel base, about 10 to about 80 percent by weight hydrating agent, and about 10 to about 50 weight percent delivered material. Alternatively, the relative weight percentages of the components of the implantable composition may have any range suitable for the particular clinical application.

In illustrative embodiments, the implantable compositions prepared utilizing the methods of the present disclosure may exhibit excellent surgical handling properties, which can range from a viscous liquid for injection (high hydrating agent content), to a hard formable material for defined hard tissue defects (low hydrating agent content), while not causing the premature degradation of contained bioactive materials associated with hydrogel carriers. Moreover, the compositions may exhibit great resistance to surgical irrigation and absence of tendency for crystallization, without a loss of osteoinductivity relative to compositions having a hydrogel carrier.

IV. Uses

The implantable compositions of the present disclosure may be used for a variety of orthopedic procedures where they participate in a bone healing/repair process through one or more mechanisms such as osteogenesis, osteoinduction, and osteoconduction (e.g., tissue grafting of either bone or soft tissue defects). The implantable compositions may be used as is, or formed into a variety of product types, such as gels, putties, pastes, cakes, sheets, etc. The implantable compositions may be used as an injectable material to fill graft sites, packed into defects, or packed into spinal cages or other devices that can hold a graft material, and may swell upon hydration to expand into a site. The implantable compositions also may be used for drug delivery or other controlled release applications. The implantable compositions can optionally be admixed with one or more substances such as adhesives, fillers, plasticizers, flexibilizing agents, biostatic/biocidal agents, surface active agents, binding and bonding agents, and the like, prior to, during, or after shaping the particles into a desired configuration. Suitable adhesives, binding agents and bonding agents include acrylic resins, cellulosics, bioresorbable polymers such as polyesters, polycarbonates, polyarylates and polyfomarates. Specifically, tyrsine, polycarbonates, tyrosine polyarylates, polyglycolides, polylactides, glycolide-lactide copolymer, etc. Suitable fillers include bone powder, demineralized bone powder, hydroxyapatite, etc. Suitable plasticizers and flexibilizing agents include liquid polyhydroxy compounds such as glycerol, monacetin, diacetin, etc. Suitable biostatic/biocidal agents include antibiotics, providone, sugars, etc. Suitable surface-active agents include the biocompatible nonionic, cationic, anionic and amphoteric surfactants. The implantable compositions may be combined with a polymer to form a biocomposite. Suitable materials for preparing biocomposites are disclosed in U.S. Patent Publication Nos. 2007/0191963, 2006/0216323, and 2005/0251267, U.S. Pat. Nos. 6,696,073, 6,478,825, 6,440,444, and 6,294,187, all herein incorporated by reference in their entireties for all purposes. The implantable materials of the present invention may be delivered alone, or inside other devices, such as cages, frames, or delivery vehicles, including but not limited to polymeric, collagen, and/or other organic or synthetic resorbable or nonresorbable fabrics or coverings. U.S. Pat. Nos. 7,323,193, 7,163,691, 6,863,694, 6,808,585. 6,616,698, 6,599,520, 6,436,138, 5,676,146, 5,510,396, 5,507,813, 5,484,601, 5,439,684, 5,405,390, 5,314,476, 5,298,254, 5,290,558, 5,284,655, 5,236,456, 5,073,373, U.S. Patent Application Publications Nos. 2007/0098756, 2007/0110820; 2007/0154563; 2009/0130173, and 2009/0192474 and U.S. patent application Ser. Nos. 12/171,168; 12/205,539; 12/140,062; 12/267,985; 12/140,025; 12/267,985; 12/254,619; 61/108,350, 61/152,057; 61/154,673; 61/154,679, and 61/154,689 also are herein incorporated by reference in their entireties.

The implantable compositions of the present disclosure may be subjected to a configuring step to form an implant. The configuring step can be employed using conventional equipment known to those skilled in the art to produce a wide variety of geometries, e.g., concave or convex surfaces, stepped surfaces, cylindrical dowels, wedges, blocks, screws, and the like. A surgically implantable material fabricated from elongated bone particles that have been demineralized, which may be shaped as a sheet, and processes for fabricating shaped materials from demineralized bone particles are disclosed in U.S. Pat. Nos. 5,507,813 and 6,436,138, respectively, the contents of which are incorporated by reference herein. Suitable sheets include those sold under the trade name Grafton® DBM Flex, which must be wetted/hydrated prior to use to be useful for implantation. Such sheets have recently been reported as effective in seeding human bone marrow stromal cells, which may be useful in the repair of large bone defects. Kasten et al., "Comparison of Human Bone Marrow Stromal Cells Seeded on Calcium-Deficient Hydroxyapatite, Betatricalcium Phosphate and Demineralized Bone Matrix," *Biomaterials*, 24(15):2593-603, 2003.

The implantable compositions of the present disclosure may assume a determined or regular form or configuration such as a sheet, plate, disk, tunnel, cone, or tube, etc. Prefabricated geometry may include, but is not be limited to, a crescent apron for single site use, an I-shape to be placed between teeth for intra-bony defects, a rectangular bib for defects involving both the buccal and lingual alveolar ridges, neutralization plates, reconstructive plates, buttress plates, T-buttress plates, spoon plates, clover leaf plates, condylar plates, compression plates, bridge plates, or wave plates. Partial tubular as well as flat plates can be fabricated from the osteoimplant. Such plates may include such conformations as, e.g., concave contoured, bowl shaped, or defect shaped. The implantable compositions can be machined or shaped by any suitable mechanical shaping means. Computerized modeling can provide for the intricately-shaped three-dimensional architecture of an implantable compositions customfitted to the bone repair site with great precision.

V. Examples

Example 1

Viscous chitosan solutions were prepared as follows:

100 ml of deionized water was measured out. 3 g of citric acid anhydrous was added to the deionized water. 3 g of chitosan was added and the mixture stirred by hand until dissolved and a viscous solution resulted. Following the addition of chitosan, a hydrating agent (glycerol, high PEG (35,000 MW), low PEG (20,000 MW), or PEG liquid (600 MW)), and a bioactive component (re-mineralized DBM powder or demineralized powder) were added to the viscous solution. Table 1 below describes amounts of hydrating agent and bioactive component added to each preparation. Following the addition of hydrating agent and bioactive component, the compositions were frozen at −70° C. for about 6 hours, then lyophilized using a program that started at −54° C. and warmed to 35° C. The total cycle length was 48 hours, but the material can be dried using alternative temperatures and cycle lengths, for example using a 35 degree heat cycle for 24 hours.

spinal cages or other implants that can hold a graft material, and will generally swell upon hydration to expand in a site. It was further observed that compositions exhibiting hard material properties (higher loading of bioactive material such as DBM) may be molded into specific shapes that may facilitate use in spinal cages as fillers, deep screw holes, etc. and will swell upon hydration to fill a site. Such compositions further may be useful in controlled release drug delivery applications.

Example 2

Samples were prepared as follows. A starch was hydrated with water. The hydrated starch was mixed with glycerol.

TABLE 1

| Component | Amount/Prep. # A | B | C | D | E | F | G |
|---|---|---|---|---|---|---|---|
| Viscous chitosan solution | 16 g | 16 g | 16 g | 14 g | 14 g | 14 g | 14 g |
| Glycerol | 3.32 g | 5.16 g | 7.00 g | 7.04 g | 6.03 g | 5.01 g | 4.18 g |
| PEG - 35,000 MW | — | — | — | — | — | — | — |
| PEG - 20,000 MW | — | — | — | — | — | — | — |
| PEG liquid - 600 MW | — | — | — | — | 1.04 g | 2.03 g | 3.63 g |
| Re-mineralized DBM powder | 3 g | — | — | — | — | — | — |
| Demineralized powder | — | — | — | 0.71 g | 0.71 g | 0.71 g | 0.71 g |

| Component | H | I | J | K | L |
|---|---|---|---|---|---|
| Viscous chitosan solution | 14 g | 14 g | 16 g | 16 g | 16 g |
| Glycerol | 1.45 g | — | 3.61 g | 5.35 g | 7.11 g |
| PEG - 35,000 MW | — | — | 0.5 g | 0.5 g | 0.5 g |
| PEG - 20,000 MW | — | — | 0.5 g | 0.5 g | 0.5 g |
| PEG liquid - 600 MW | 6.11 g | 7.13 g | — | — | — |
| Re-mineralized DBM powder | — | — | 3 g | 3 g | 3 g |
| Demineralized powder | 0.71 g | 0.71 g | — | — | — |

Table 2 includes the observations made with respect to each of the preparations of Table 1.

| Preparation number | Properties |
|---|---|
| A | Flexible adhesive cake upon lyophilization; swells in water by about 3x; does not disintegrate |
| B | Flexible adhesive cake upon lyophilization; swells in water by about 3x; does not disintegrate |
| C | Flexible adhesive cake upon lyophilization; swells in water by about 3x; does not disintegrate; less slimy than lower glycerol content preparations |
| D | Flexible adhesive cake upon lyophilization; swells in water by about 3x; does not disintegrate |
| E | Flexible adhesive cake upon lyophilization; swells in water by about 3x; does not disintegrate |
| F | Flexible adhesive cake upon lyophilization; swells in water by about 3x; does not disintegrate |
| G | Flexible adhesive cake upon lyophilization; swells in water by about 3x; does not disintegrate |
| H | Flexible adhesive cake upon lyophilization; swells in water by about 3x; very weak upon handling |
| I | Flexible adhesive cake upon lyophilization; disintegrates in water |
| J | Flexible adhesive cake upon lyophilization; swells in water by about 3x; does not disintegrate |
| K | Flexible adhesive cake upon lyophilization; swells in water by about 3x; does not disintegrate |
| L | Flexible adhesive cake upon lyophilization; swells in water by about 3x; does not disintegrate |

It was observed that the compositions with viscous liquid properties use a higher polyhydroxy content and may be used as injectable materials to fill graft sites. It was also observed that compositions having gel or flexible properties may be packed into defects, packed into delivery vehicles such as Thereafter, DBM particles (same as Gel; 106 to 500 microns) were added to the hydrated starch-glycerol mixture. The resulting product was lyophilized. Lyophilization allowed the glycerol to nearly completely replace the water in the starch. Testing of a sample containing 56% glycerol by weight showed a water content of only 0.53%, making the formulation about 29% bone and 71% nonaqueous carrier.

Handling Properties

The handling properties of the resulting compositions at least partially depend on the amount of glycerol in the composition. For example, a sample composition containing 55% glycerol was flowable, while a sample containing 49% glycerol had stiff, putty-like qualities.

Irrigation

The samples were tested for resistance to irrigation compared to glycerol gel and paste analogues [We should include details relating to the specifics of those compositions. In general, Gel and Putty are 20 to 30% bone and 70 to 80% glycerol. Gel is flowable, Putty is stiffer. However, Putty has long fibers that tangle together to make a cohesive product, and Gel is just particles. In comparison, the starch-glycerol products showed great resistance to irrigation, making it suitable for other applications.

Stability

A sample composition containing 49% glycerol was stored in ambient conditions for 5 months. After 5 months, its handling properties were substantially unchanged and there was no sign of crystallization. Additionally, there was no sign of mold grown, which would be expected with a water-based formulation.

Example 3

Osteoinductivity testing was carried out on 4 different samples, all of which were made from the same R&D donor DBM. The samples were: control DBM powder; DBM in starch-glycerol carrier containing about 49% glycerol to yield a stiff paste; alginate-glycerol DBM formulation; and a hyaluronic acid-starch DBM formulation. The latter two materials were made up using the same procedures as the starch-glycerol formulation. A small preliminary athymic model study was designed and carried out to observe any preliminary effects of these 3 anhydrous carriers on osteoinductivity. According to histology and pCT Bone/Nodule calculations, all three carriers performed well (with typical animal variability) in comparison to the control, which itself scored an average of 2.5. The same lot of donor DBM had been used previously yielding an osteoinductivity score of 2, so was considered to be a mid-range control. Starch-glycerol and alginate-glycerol performed identically with an average osteoinductivity score of 1.75, while hyaluronic acid-glycerol performed better with an average osteoinductivity score of 2.00 Table 3 below summarizes the randomization and calculations.

TABLE 3*

| Study # | Animal | LIM | % Bone | OI Score | RIM | % Bone | OI Score | Impl Time |
|---|---|---|---|---|---|---|---|---|
| 10-004 | 1 | CON | 38.0 | 3 | STG | 32.3 | 3 | 28 |
| 10-004 | 2 | ALG | 32.2 | 3 | HAG | 27.0 | 3 | 28 |
| 10-004 | 3 | STG | 6.5 | 1 | ALG | 3.1 | 1 | 28 |
| 10-004 | 4 | HAG | 17.0 | 2 | CON | 29.0 | 3 | 28 |
| 10-004 | 5 | ALG | 16.2 | 2 | STG | 37.3 | 2 H | 28 |
| 10-004 | 6 | CON | 25.3 | 2 | ALG | 6.3 | 1 H | 28 |
| 10-004 | 7 | STG | 14.7 | 1 H | HAG | 13.1 | 2 | 28 |
| 10-004 | 8 | HAG | 5.6 | 1 | CON | 17.1 | 2 | 28 |

*STG (Starch/Glycerol), ALG (Alginate/Glycerol), HAG (Hyaluronic Acid/Glycerol)
Athymic study results in comparison to the control bone (no carrier present) (H denotes it was scored in the higher realm of the classification)

The handling characteristics are vastly improved and in the currently tested paste formulation, the shelf life lengthened considerably with the elimination of water and the presence of glycerol to act as an antimicrobial.

The invention claimed is:

1. A method for preparing an implantable composition comprising:
   (i) providing a gel base comprising alginate and dextran;
   (ii) adding water, citric acid anhydrous and a hydrating agent to the gel base to form a mixture;
   (iii) reducing the water content of the mixture; and
   (iv) adding a delivered material before, during, and/or after step (ii) or (iii);
   wherein the water content is reduced to about 5%, about 3% or about 1% by weight of the implantable composition.

2. The method of claim 1, wherein the delivered material includes or comprises a bioactive compound and/or a biocompatible compound.

3. The method of claim 1, wherein the gel base further comprises chitosan, hyaluronic acid, polyvinyl alcohol, polyvinyl pyrrolidone, carboxymethyl cellulose, collagen, gelatin, an extracted proteins, a starch, or combinations thereof.

4. The method of claim 3, wherein the gel base comprises chitosan.

5. The method of claim 1, wherein the hydrating agent comprises a polyhydroxy compound.

6. The method of claim 5, wherein the polyhydroxy compound is selected from the group consisting of glycerol, low molecular weight polyethylene glycol, high molecular weight polyethylene glycol, or combinations thereof.

7. The method of claim 1, wherein the step of adding a delivered material comprises adding a bioactive material.

8. The method of claim 7, wherein the bioactive material comprises at least one osteogenic and/or osteoinductive material.

9. The method of claim 8, wherein the osteogenic and/or osteoinductive material comprises demineralized bone.

10. The method of claim 1, wherein the step of reducing the water content comprises subjecting the composition to lyophilization.

11. The method of claim 10, wherein the water content is reduced to about 3% by weight of the implantable composition.

12. The method of claim 11, wherein the water content is reduced to about 1% by weight of the implantable composition.

13. An implantable composition comprising:
    a delivered material, and
    a carrier comprising:
    a gel base comprising alginate and dextran;
    a hydrating agent; and
    citric acid anhydrous;
    wherein a water content of the implantable composition is about 5%, about 3%, or about 1% by weight of the composition.

14. The implantable composition of claim 13, wherein the delivered material includes or comprises a bioactive compound and/or a biocompatible compound.

15. The implantable composition of claim 14, wherein the bioactive material comprises at least one osteogenic and/or osteoinductive material.

16. The implantable composition of claim 15, wherein the osteogenic and/or osteoinductive material comprises demineralized bone.

17. The implantable composition of claim 13, wherein the gel base further comprises chitosan, hyaluronic acid, polyvinyl alcohol, polyvinyl pyrrolidone, carboxymethyl cellulose, collagen, gelatin, an extracted proteins, a starch, or combinations thereof.

18. The implantable composition of claim 17, wherein the gel base comprises chitosan.

19. The implantable composition of claim 13, further comprising an additive encapsulated within biodegradable nanospheres.

* * * * *